(12) United States Patent
DeLuca et al.

(10) Patent No.: US 8,178,517 B2
(45) Date of Patent: May 15, 2012

(54) 6-METHYLVITAMIN $D_3$ ANALOGS AND THEIR USES

(75) Inventors: Hector F. DeLuca, Deerfield, WI (US);
Katarzyna Sokolowska, Lomza (PL);
Lori A. Plum, Arena, WI (US);
Margaret Clagett-Dame, Deerfield, WI (US); Rafal R. Sicinski, Warsaw (PL);
Antonio Mouriño, Ames (ES)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 12/895,577

(22) Filed: Sep. 30, 2010

(65) Prior Publication Data

US 2011/0082123 A1     Apr. 7, 2011

Related U.S. Application Data

(60) Provisional application No. 61/248,129, filed on Oct. 2, 2009.

(51) Int. Cl.
*A61K 31/59* (2006.01)
*C07D 401/00* (2006.01)
(52) U.S. Cl. ........................................ 514/167; 552/653
(58) Field of Classification Search .................. 514/167; 552/653
See application file for complete search history.

(56) References Cited

U.S. PATENT DOCUMENTS 5,843,928 A * 12/1998 Deluca et al. .................. 514/167

OTHER PUBLICATIONS

Addo, J.K. et al; C-6 functionalized analogs of 25-hydroxyvitamin d3 and 1alpha,25-dihydroxyvitamin d3: Synthesis and binding analysis with vitamin D-binding protein and vitamin D receptor; Steroids; pp. 273-282; 1999.
Kaya, T. et al; Covalent labeling of nuclear vitamin D receptor with affinity labeling reagents containing a cross-linking probe at three different positions of the parent ligand: Structural and biochemical implications; Bioorganic Chemistry; pp. 57-63; 2009.
Sokolowski, K., et al; Synthesis and biological evaluation of 6-methyl analog of 1alpha,25-dihydroxyvitamin D3; Journal of Steroid Biochemistry & Molecular Biology; pp. 121; 2010.
International Search Report and Written Opinion; PCT International Application No. PCT/US2010/05989; mailed Apr. 26, 2011.
XP002629980; Database CA [Online]; Chemical Abstracts Service, Columbus, Ohio, US; Takenouchi, Kazuya et al: "6,7-Substituted 19-norvitamin D3 derivatives and pharmaceuticals containing them"; retrieved from STN Database accession No. 2004:507806 abstract.
XP002629981; Database WPI Week 200445; Thomson Scientific, London, GB; AN2004-472141; & JP 2004 175763 A (Teijin Ltd) Jun. 24, 2004 abstract.

* cited by examiner

*Primary Examiner* — Sabiha Qazi
(74) *Attorney, Agent, or Firm* — Andrus, Sceales, Starke & Sawall, LLP

(57) ABSTRACT

This invention discloses 6-methylvitamin $D_3$ analogs, and specifically 1α,25-dihydroxy-6-methylvitamin $D_3$, and pharmaceutical uses therefor. This compound exhibits vitamin D receptor binding activity and transcription activity as well as activity in arresting the proliferation of undifferentiated cells and inducing their differentiation to the monocyte thus evidencing use as an anti-cancer agent, especially for the treatment or prevention of leukemia, colon cancer, breast cancer, skin cancer or prostate cancer. This compound also exhibits low in vivo calcemic activity, but because it binds the receptor with the same affinity as the native hormone calcitriol, it may act as an antagonist to inhibit development of hypercalcemia.

29 Claims, 5 Drawing Sheets

6-METHYLVITAMIN D₃ ANALOGS AND THEIR USES

BACKGROUND OF THE INVENTION

This invention relates to vitamin D compounds, and more particularly to 6-methylvitamin $D_3$ analogs and their pharmaceutical uses.

The most active metabolite of vitamin $D_3$, $1\alpha,25$-dihydroxyvitamin $D_3$ is a potent calcium and phosphorous-regulating hormone playing an important role in bone homeostasis in animals and humans. Also, in addition to this classical role, the natural hormone elicits immunomodulation as well as cell differentiation and proliferation activities in numerous malignant cells and keratinocytes [Feldman et al, Vitamin D, $2^{nd}$ ed.; Elsevier Academic Press: New York, 2005]. $1\alpha,25$-Dihydroxyvitamin $D_3$ expresses these functions by binding to the vitamin D receptor (VDR), a ligand-regulated transcription factor. Structural analogs of this metabolite have been prepared and tested such as $1\alpha$-hydroxyvitamin $D_3$, $1\alpha$-hydroxyvitamin $D_2$, and various other side-chain and A-ring modified vitamins. Some potent synthetic analogs have been used clinically to treat bone disorders such as osteoporosis and the skin disorder—psoriasis. Some of these compounds exhibit separation of activities in cell differentiation and calcium regulation. The difference in activity may be advantageous in treating a variety of diseases such as renal osteodystrophy, vitamin D-resistant rickets, osteoporosis, psoriasis, and other malignancies.

Although more than 3000 synthetic analogs of the natural hormone have been obtained and tested to date, very few of them were characterized by substitution of the intercyclic C(5)=C(6)-C(7)=C(8) diene moiety. 6-Fluorovitamin $D_3$ was synthesized by Dauben et al. [J. Org. Chem. 50, 2007 (1985)] and this compound has been shown to antagonize $1\alpha,25$-$(OH)_2D_3$ activity, especially intestinal calcium absorption, in vivo in chicken [Wilhelm et al., Arch. Biochem. Biophys. 233, 127 (1984)]. The synthesis of 6-methylvitamin $D_3$ was reported by Sheves and Mazur [J. Chem. Soc., Chem. Commun. 21 (1977)] using 6-oxo-3,5-cyclovitamin D precursor; the same compound was also obtained by Yamada et al. [Tetrahedron Letters 22, 3085 (1981)] by reductive thermal desulfonylation of the 6-methylated vitamin $D_3$-sulfur dioxide adduct. Recently, $1\alpha$-hydroxy-6-methylvitamin $D_3$ was synthesized by a novel approach involving Pd-catalyzed carbocyclization—Negishi cross-coupling cascade [Reino et al., Org. Lett. 7, 5885 (2005)].

Compounds alkylated at C-6 seemed to be interesting targets for synthetic and biological studies. Such vitamin D analogs easily undergo thermal conversion to their previtamin forms. Moreover, the results of molecular modeling indicate that significant deviation from planarity must be present in their diene system, connecting the ring A to the C,D-hydrindane fragment. This is obviously associated with the interaction of the 6-alkyl substituent and hydrogens from the C-ring (at C-9). Such deviation from the planar geometry can be of importance when the vitamin D analog forms a complex with VDR. Recently, Moras et al. reported the X-ray crystal structure of the ligand binding domain (LBD) of the hVDR complexed with the native hormone [Moll. Cell, 5, 173 (2000)]. Later, many other crystal structures of the LBD-VDR bound to different vitamin D compounds were solved and it became clear that VDR binds (at least in the crystalline state) the vitamin D ligands having their intercyclic C(5)=C(6)-C(7)=C(8) diene moiety in the s-trans conformation, exhibiting a torsion angle of ca. −150°. Therefore, in a continuing effort to develop $1\alpha,25$-dihydroxyvitamin $D_3$ analogs with biological profiles suitable for pharmaceutical uses we have synthesized 6-methyl analog of $1\alpha,25$-dihydroxyvitamin $D_3$.

SUMMARY OF THE INVENTION

The present invention is directed toward 6-methylvitaimn $D_3$ analogs, their biological activity, and various pharmaceutical uses for these compounds. These new vitamin D compounds not known heretofore are the vitamin $D_3$ analogs having a hydroxyl substituent at the carbon-1-position (C-1), a hydroxyl substituent attached to the 25-position (C-25) in the side chain, and a methyl group attached at the 6 position (C-6). The preferred vitamin D analog is $1\alpha,25$-dihydroxy-6-methylvitaimn $D_3$ (hereinafter referred to as "Me-Cvit").

Structurally these 6-methylvitamin $D_3$ analogs are characterized by the general formula I shown below:

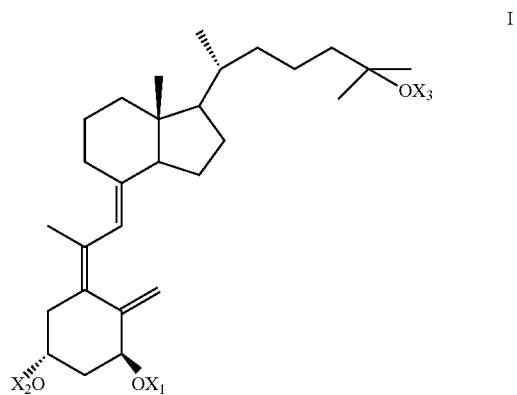

I where $X_1$, $X_2$ and $X_3$, which may be the same or different, are each selected from hydrogen or a hydroxy-protecting group. The preferred analog is $1\alpha,25$-dihydroxy-6-methylvitamin $D_3$ which has the following formula Ia:

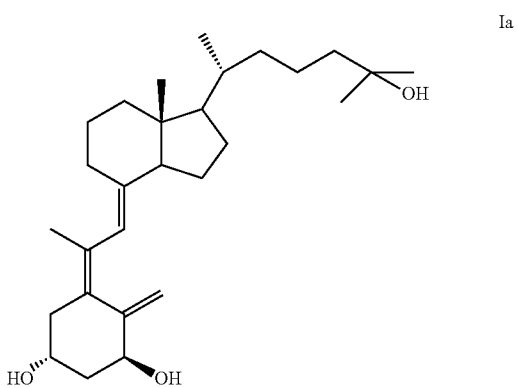

Ia

The above compounds I, particularly Ia, exhibit a desired, and highly advantageous, pattern of biological activity. These compounds are characterized by relatively high binding to vitamin D receptors, which is about the same as that of the native hormone $1\alpha,25$-dihydroxyvitamin $D_3$. These compounds are less potent (about 2 logs) in causing cellular differentiation and are also less potent (about one log) in stimulating 24-OHase gene expression compared to 1,25 $(OH)_2D_3$. These compounds also have less ability to promote intestinal calcium transport in vivo than $1,25(OH)_2D_3$, especially at the recommended lower doses. They are greater than 1,000 times less potent than the native hormone, and thus would be classified as having lower activity and thus lower potency in vivo in stimulating intestinal calcium transport activity, as compared to that of 1α,25-dihydroxyvitamin $D_3$. These compounds I, and particularly Ia, also have less ability to mobilize calcium from bone, and they are about 400 times less potent than the native hormone, and thus would be classified as having lower potency in vivo in bone calcium mobilizing activity as compared to 1α,25-dihydroxyvitamin $D_3$.

The above compounds I, and particularly Ia, are characterized by relatively high cell differentiation activity and in promoting transcription of the 24-hydroxylase gene. Thus, because these compounds have cellular differentiation activity and are more potent than the native hormone in causing transcription, but are less potent in causing intestinal calcium transport, they have potential as an anti-cancer agent, especially for the prevention or treatment of leukemia, colon cancer, breast cancer, skin cancer and prostate cancer. Also, because compounds of formula I, and especially the compound Me-Cvit of formula Ia, bind to the Vitamin D receptor with the same affinity as the native hormone but has markedly lower potency in biological calcemic activities downstream from receptor binding, it is possible this compound could act as a dominant negative and be useful as an antidote for vitamin D intoxication, i.e. it may act in vivo as an antagonist against hypercalcemia caused by a vitamin D compound.

One or more of the compounds may be present in a composition to treat the above-noted diseases in an amount from about 0.01 μg/gm to about 1000 μg/gm of the composition, preferably from about 0.1 μg/gm to about 500 μg/gm of the composition, and may be administered topically, transdermally, orally, rectally, nasally, sublingually or parenterally in dosages of from about 0.01 μg/day to about 1000 μg/day, preferably from about 0.1 μg/day to about 500 μg/day.

BRIEF DESCRIPTION OF THE DRAWINGS

In the drawings:

FIG. 1 is a graph illustrating the relative activity of Me-Cvit and 1,25(OH)$_2$D$_3$ to compete for binding with [$^3$H]-1,25-(OH)-2-$D_3$ to the full-length recombinant rat vitamin D receptor;

FIG. 2 is a graph illustrating the percent HL-60 cell differentiation as a function of the concentration of Me-Cvit and 1,25(OH)$_2$D$_3$;

FIG. 3 is a graph illustrating the in vitro transcription activity of 1,25(OH)$_2$D$_3$ as compared to Me-Cvit;

FIG. 4 is a graph illustrating the bone calcium mobilization activity of 1,25(OH)$_2$D$_3$ as compared to Me-Cvit in a group of animals; and FIG. 5 is a graph illustrating the intestinal calcium transport activity of 1,25(OH)$_2$D$_3$ as compared to Me-Cvit in a group of animals.

DETAILED DESCRIPTION OF THE INVENTION

Figure 1:
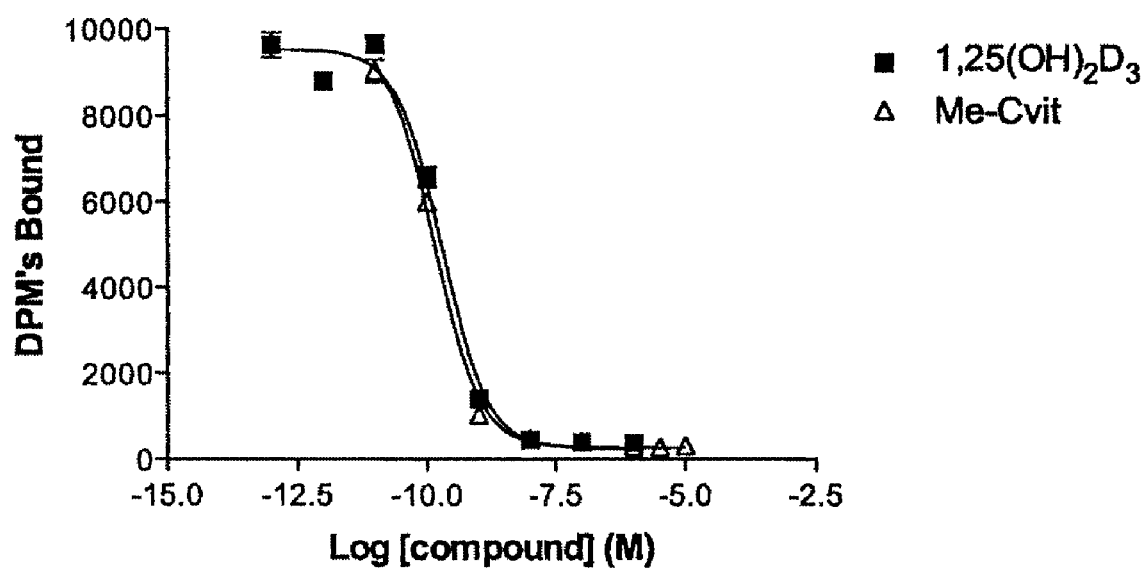
FIGS. 1-5 illustrate various biological activities of 1α,25-dihydroxy-6-methylvitamin $D_3$, hereinafter referred to as "Me-Cvit", as compared to the native hormone 1α,25-dihydroxyvitamin $D_3$, hereinafter "1,25(OH)$_2$D$_3$."

1α,25-dihydroxy-6-methylvitamin $D_3$ (referred to herein as "Me-Cvit") a vitamin D analog which is characterized by the presence of a methylene substituent at the carbon 1 (C-1), a hydroxyl substituent attached to the 25-position (C-25) in the side chain, and a methyl group attached at the 6 position (C-6), was synthesized and tested. Structurally, this vitamin D analog is characterized by the general formula Ia previously illustrated herein, and its pro-drug (in protected hydroxy form) is characterized by general formula I previously illustrated herein.

The preparation of 6-methylvitamin $D_3$ analogs having the structure I can be accomplished by a common general method, i.e. the coupling of a bicyclic vinyl bromide II, easily prepared from a Grundmann ketone III, with the acyclic unit, vinyl triflate IV, followed by deprotection at C-1, C-3 and C-25 in the latter compound to arrive at the compound Me-Cvit having the structure Ia (see Scheme 1 herein):

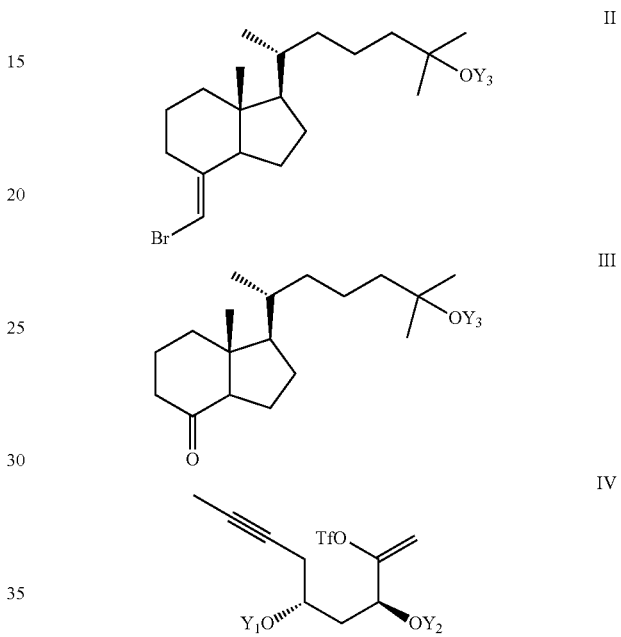

In the structures II, III and IV groups $Y_1$, $Y_2$ and $Y_3$ are selected from the group consisting of hydrogen and a hydroxy-protecting group. The method shown above represents an application of a new, highly efficient convergent strategy in which ring A and the triene unit of the vitamin D compound are constructed by one-pot Pd-catalyzed tandem cyclization-Negishi coupling process. Such strategy has been applied effectively for the preparation of the 1α-hydroxyvitamin $D_3$ and 1α,25-dihydroxyvitamin $D_3$ [Reino et al., Org. Lett. 7, 5885 (2005)].

Hydrindanones of the general structure III are known, or can be prepared by known methods. Specific important example of such known bicyclic ketones is 25-hydroxy Grundmann's ketone [Baggiolini et al., J. Org. Chem., 51, 3098 (1986)]. Bromoolefines of the general structure II are known [for $Y_3$=TES, see: Maeyama et al., Heterocycles 70, 295 (2006)] or can be prepared from III according to Trost procedure [J. Am. Chem. Soc. 114, 1924, 9836 (1992)].

Vinyl triflates of the general structure IV are known, or can be prepared by known methods [Reino et al., Org. Lett. 7, 5885 (2005)].

For the preparation of the required vitamin D compounds of general structure I, a synthetic route has been developed starting from the known alkenyl bromide 1 [Maeyama et al., Heterocycles 70, 295 (2006)] and the known vinyl triflate 2 [Reino et al., Org. Lett. 7, 5885 (2005)]. Process of their coupling and further transformation into the desired 1α,25-dihydroxy-6-methylvitamin $D_3$ is shown on the SCHEME I. Thus, metalation of the bromide 1 with tert-butyllithium and subsequent transmetalation with zinc bromide provided the intermediate organozinc derivative. To this derivative was added the vinyl triflate 2 together with triethylamine and a catalytic amount of tetrakis(triphenylphosphine)palladium (0). Removal of the silyl protecting groups in the obtained 6-methylvitamin 3 was performed in the acidic conditions using hydrofluoric acid-pyridine complex. The final 1α,25-dihydroxy-6-methylvitamin $D_3$ (4) was purified by HPLC. Although the vitamin 4 very easily isomerizes to its previtamin D form 5, it can be stored by a prolonged time in a freezer.

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. "Alkoxy" refers to any alkyl radical which is attached by oxygen, i.e. a group represented by "alkyl-O." Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively. An "alkylidene" refers to a radical having the general formula $C_kH_{2k}$— where k is an integer.

More specifically, reference should be made to the following illustrative example and description as well as to Scheme 1 herein for a detailed illustration of the preparation of compound Me-Cvit.

In this example specific products identified by Arabic numerals (1, 2, 3, etc.) refer to the specific structures so identified in the Scheme 1.

EXAMPLES

Chemistry. Ultraviolet (UV) absorption spectra were recorded with a Perkin-Elmer Lambda 313 UV-VIS spectrophotometer in ethanol. $^1$H nuclear magnetic resonance (NMR) spectra were recorded in deuteriochloroform at 400 and 500 MHz with a Bruker DMX-400 and Bruker DMX-500 spectrometers, respectively. $^{13}$C nuclear magnetic resonance (NMR) spectra were recorded at 100 and 125 MHz with the same spectrometers in deuteriochloroform. Chemical shifts (δ) were reported downfield from internal Me$_4$Si (δ 0.00). High-performance liquid chromatography (HPLC) was performed on a Waters Associates liquid chromatograph equipped with a Model 6000A solvent delivery system, a Model U6K Universal injector, and a Model 486 tunable absorbance detector. THF was freshly distilled before use from sodium benzophenone ketyl under argon.

Example 1

Preparation of 1α,25-dihydroxy-6-methylvitamin $D_3$ (4)

(a) Coupling of alkenyl bromide 1 with vinyl triflate 2 (SCHEME I). A solution of t-BuLi (1.55 M in pentane; 0.31 mL, 0.466 mmol) was added dropwise to a solution of vinyl bromide 1 (100 mg, 0.210 mmol) in anhydrous THF (2 mL) at −78° C. under argon. After 30 min, a solution of ZnBr$_2$ (0.48 M in THF; 0.53 mL, 0.252 mmol) was added. The reaction mixture was stirred at 0° C. for 1 h. After cooling to −40° C., a mixture of vinyl triflate 2 (90 mg, 0.146 mmol), Et$_3$N (0.13 mL, 1.05 mmol) and (Ph$_3$P)$_4$Pd (14 mg, 0.012 mmol) in anhydrous THF (2 mL) was transferred via cannula. The mixture was stirred at room temperature for 14 h. Then it was quenched by addition of water, poured into saturated aqueous solution of NH$_4$Cl and diluted with ether. Organic phase was dried (Na$_2$SO$_4$) and concentrated. The residue was purified by flash chromatography on silica. Elution with hexane/Et$_2$O (98:2) provided the crude product that was purified by HPLC (9.4 mm×25 cm Zorbax-Sil column, 4 mL/min) using hexane. The protected 6-methyl analog of the natural hormone (compound 3) was eluted at R$_V$ 15 mL (61 mg, 49%; 88% based on recovered substrate).

3: $^1$H NMR (500 MHz, CDCl$_3$) δ 5.68 (1H, s, 7-H), 5.21 (1H, d, J=0.5 Hz, 19E-H), 4.79 (1H, d, J=1.6 Hz, 19Z-H), 4.54 (1H, dd, J=9.0 and 4.0 Hz, 1□-H), 4.32 (1H, br s, 3□-H), 2.55 (1H, m), 2.26 (1H, m), 1.90 (1H, m), 1.83 (3H, s, 6-CH$_3$), 1.19 (6H, s, 26- and 27-H$_3$), 1.06 (36H, 6×SiCH(CH$_3$)$_2$], 0.95 (9H, t, J=7.9 Hz, 3×SiCH$_2$CH$_3$), 0.93 (3H, d, J=6.2 Hz, 21-H$_3$), 0.88 (6H, m, 6×SiCH(CH$_3$)$_2$), 0.56 (s, 3H, 18-H$_3$), 0.56 (6H, q, J=7.9 Hz, 3×SiCH$_2$CH$_3$); $^{13}$C NMR (125 MHz) δ 150.9 (s, C-10), 138.5 (s, C-8), 132.6 (s, C-5), 129.2 (s, C-6), 124.1 (d, C-7), 110.7 (t, C-19), 73.5 (s, C-25), 70.6 (d, C-1), 68.0 (d, C-3), 56.6 (d), 55.9 (d), 45.5 (t), 40.6 (t), 39.1 (t), 36.5 (t), 36.2 (d), 31.6 (t), 30.5 (t), 30.0 and 29.8 (2×q, C-26 and C-27), 27.7 (t), 25.3 (s), 23.5 (t), 22.7 (t), 22.5 (t), 20.9 (t), 20.3 (q, 6-CH$_3$), 18.8 (q, C-21), 18.27, 18.2, 18.18, 18.15, 18.12 and 18.1 (6×q, CH$_3$-TIPS), 12.4 and 12.3 (2×d, CH-TIPS), 11.9 (q, C-18), 7.1 (q, SiCH$_2$CH$_3$), 6.8 (t, SiCH$_2$CH$_3$).

(b) Hydroxyls deprotection in the silylated vitamin 3. A solution of HF-pyridine complex (ca 70% HF, 0.1 mL) was added dropwise to a solution of protected 6-methylvitamin 3 (37 mg, 0.086 mmol) in CH$_3$CN (0.5 mL), CH$_2$Cl$_2$ (0.25 mL) and Et$_3$N (0.25 mL) at 0° C. The reaction mixture was stirred at room temperature for 20 min. Next portion of HF-pyridine complex (0.2 mL) was added during 1 h and the mixture was stirred at room temperature for 2 h. The reaction was cooled to 0° C., quenched by slow addition of saturated aqueous solution of NaHCO$_3$, and diluted with AcOEt. Organic phase was washed with saturated aqueous solution of NaHCO$_3$, dried (Na$_2$SO$_4$) and concentrated. The residue applied on Sep-Pak (2 g) and eluted with hexane/AcOEt (3:7). The product was then purified by HPLC (9.4 mm×25 cm Zorbax-Sil column, 4 mL/min) using hexane/2-propanol (8:2) solvent system and 1α,25-dihydroxy-6-methylvitamin $D_3$ (4) was eluted at R$_V$ 31 mL (16 mg, 86%).

4: UV (in EtOH) λ$_{max}$ 240.0 nm; $^1$H NMR (400 MHz, MeOD) δ 5.71 (1H, s, 7-H), 5.15 (1H, br s, 19-H), 4.79 (1H, d, J=1.7 Hz, 19-H), 4.34 (1H, m, 1□-H); 4.13 (1H, m, 3□-H), 2.56 (1H, br d, J=11 Hz, 9□-H), 2.43 (1H, br s), 2.03 (1H, br d), 1.88 (3H, s, 6-CH$_3$), 1.18 (6H, s, 26- and 27-H$_3$), 0.97 (3H, d, J=6.3 Hz, 21-H$_3$), 0.61 (3H, s, 18-H$_3$).

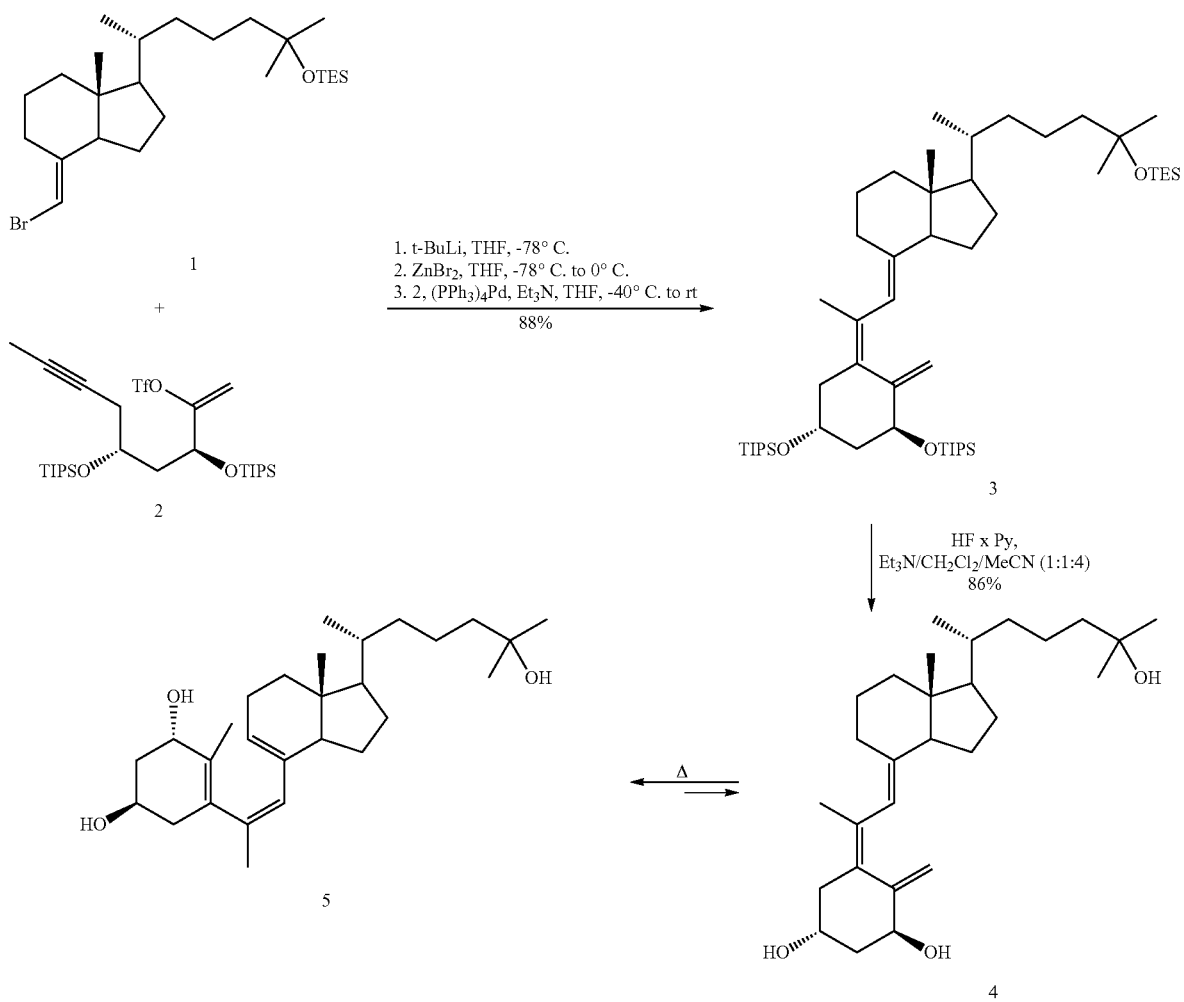

SCHEME I

Biological Activity of
1α,25-Dihydroxy-6-Methylvitamin $D_3$ Analog 4,
ME-Cvit

The introduction of a methyl group to the 6-position, as well as a hydroxyl substituent attached to the 25-position (C-25) in the side chain, and having another hydroxyl substituent located at the 1-position (C-1) of the vitamin $D_3$ compound had little effect on binding of Me-Cvit to the full length recombinant rat vitamin D receptor, as compared to 1α,25-dihydroxyvitamin $D_3$. The compound Me-Cvit bound with the same affinity to the nuclear vitamin D receptor as compared to the standard 1,25-$(OH)_2D_3$ (FIG. 1). It might be expected from these results that compound Me-Cvit would have equivalent biological activity. Surprisingly, however, compound Me-Cvit is a highly selective analog with unique biological activity.

Figure 5:
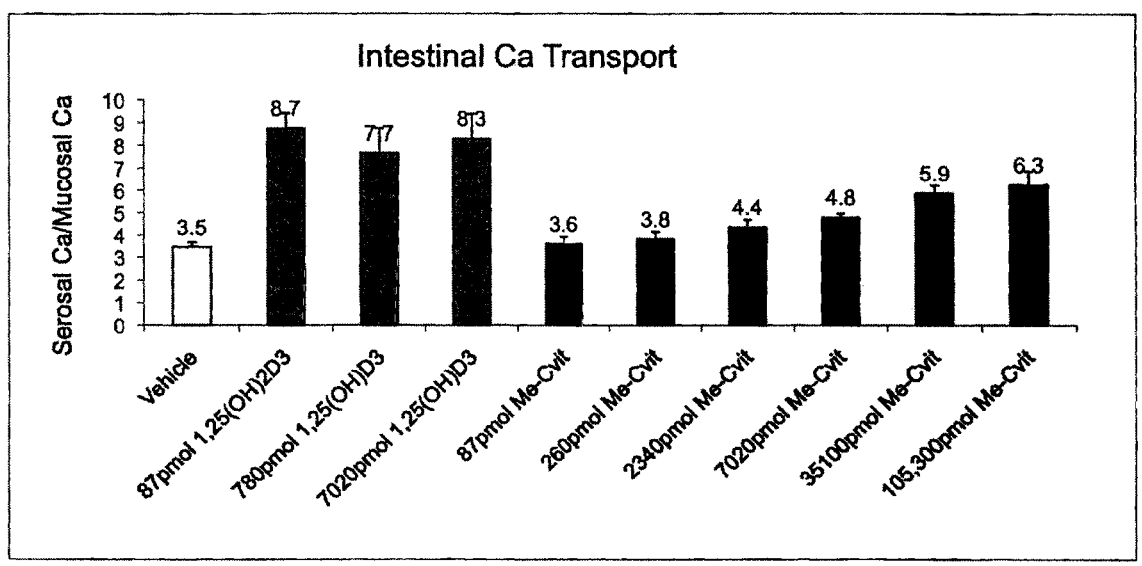

FIG. 5 shows that Me-Cvit has relatively low ability to increase intestinal calcium transport activity in vivo at low dosages. It clearly has lower potency in vivo (greater than 1,000 times less potent) as compared to that of 1,25-dihydroxyvitamin $D_3$ (1,25$(OH)_2D_3$), the natural hormone, in stimulating intestinal calcium transport, especially at the recommended lower doses.

Figure 4:
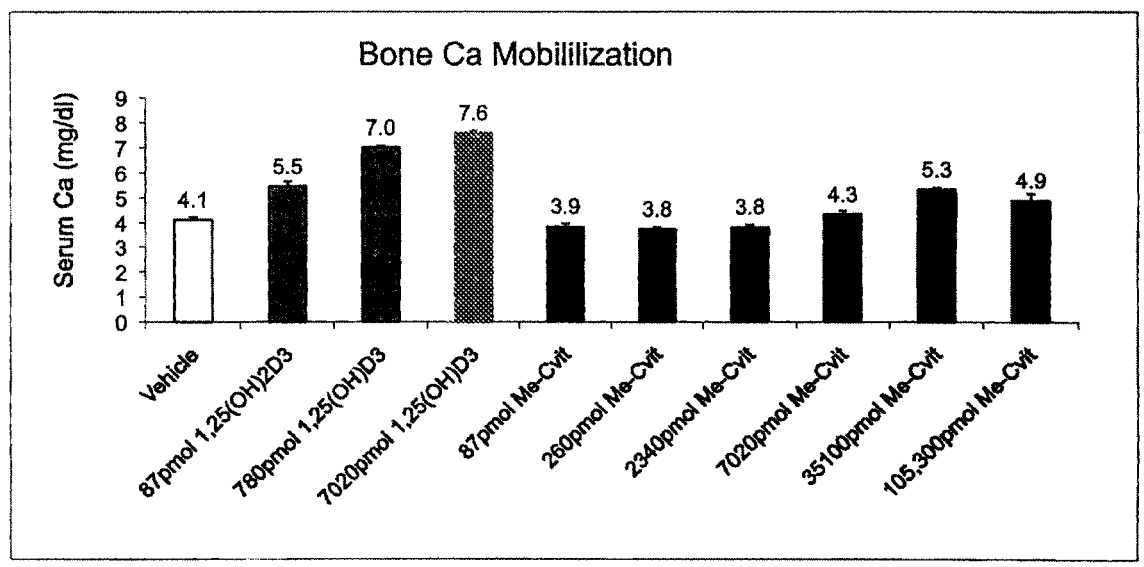

FIG. 4 demonstrates that Me-Cvit also has low bone calcium mobilization activity, as compared to 1,25$(OH)_2D_3$. Me-Cvit demonstrated less bone calcium mobilization activity than 1,25$(OH)_2D_3$ (4.3 mg/dL of Me-Cvit versus 7.6 mg/dL of 1,25$(OH)_2D_3$ at 7020 pmol dosage). Thus, Me-Cvit clearly is less effective in mobilizing calcium from bone as compared to 1,25$(OH)_2D_3$.

FIGS. 4 and 5 thus illustrate that Me-Cvit may be characterized as being less potent than 1,25$(OH)_2D_3$ in promoting intestinal calcium transport activity, and also less potent than 1,25$(OH)_2D_3$ in promoting bone calcium mobilization activity.

Figure 2:
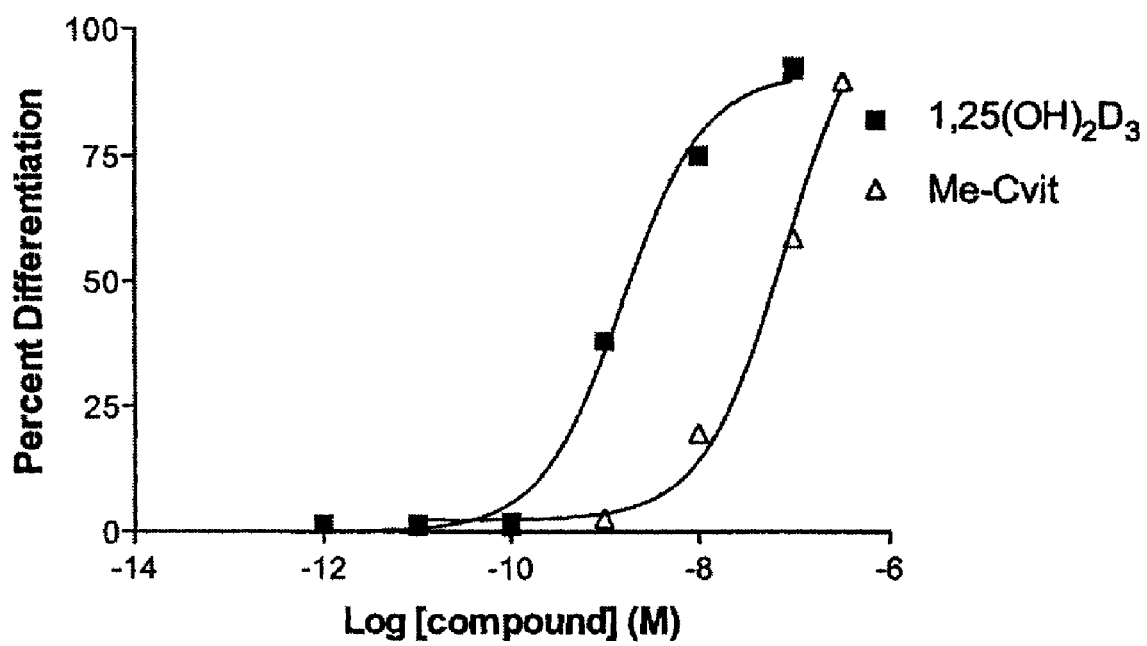

FIG. 2 illustrates that Me-Cvit is only about 2 logs or 20 times less potent than 1,25$(OH)_2D_3$ on HL-60 cell differentiation, i.e. causing the differentiation of HL-60 cells into monocytes. Thus, Me-Cvit may be a candidate for the treatment of a cancer, especially against leukemia, colon cancer, breast cancer, skin cancer and prostate cancer.

Figure 3:
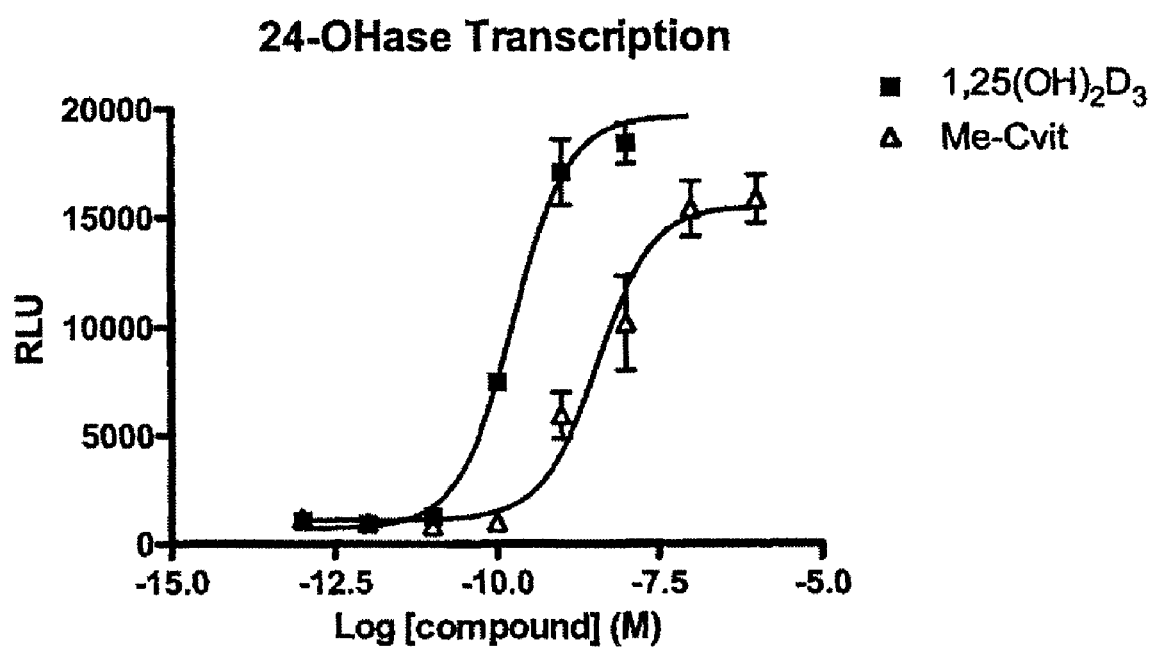

FIG. 3 illustrates that in bone cells the compound Me-Cvit is only about 1 log or 10 times less potent than 1,25$(OH)_2D_3$ in increasing transcription of the 24-hydroxylase gene. This result, together with the cell differentiation activity of FIG. 2, suggests that Me-Cvit may be effective in treating the above referred to cancers because it has direct cellular activity in causing cell differentiation, gene transcription, and in suppressing cell growth.

Also, because Me-Cvit binds the receptor with the same affinity as the native hormone but has markedly lower potency in biological calcemic activities downstream from receptor binding, it is possible this compound could act as a dominant negative and be useful as an antidote for vitamin D or analog intoxication. In other words, Me-Cvit may act in vivo as an antagonist against hypercalcemia caused by a vitamin D compound.

Experimental Methods

Vitamin D Receptor Binding
Test Material
Protein Source

Full-length recombinant rat receptor was expressed in *E. coli* BL21 (DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in $TEDK_{50}$ (50 mM Tris, 1.5 mM EDTA, pH 7.4, 5 mM DTT, 150 mM KCl) with 0.1% Chaps detergent. The receptor protein and ligand concentration were optimized such that no more than 20% of the added radiolabeled ligand was bound to the receptor.

Study Drugs

Unlabeled ligands were dissolved in ethanol and the concentrations determined using UV spectrophotometry (1,25 $(OH)_2D_3$: molar extinction coefficient=18,200 and $\lambda_{max}$=265 nm; Analogs: molar extinction coefficient=42,000 and $\lambda_{max}$=252 nm). Radiolabeled ligand (3H-1,25$(OH)_2D_3$, ~159 Ci/mmole) was added in ethanol at a final concentration of 1 nM.

Assay Conditions

Radiolabeled and unlabeled ligands were added to 100 mcl of the diluted protein at a final ethanol concentration of ≦10%, mixed and incubated overnight on ice to reach binding equilibrium. The following day, 100 mcl of hydroxylapatite slurry (50%) was added to each tube and mixed at 10-minute intervals for 30 minutes. The hydroxylapaptite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation
Test Material
Study Drugs

The study drugs were dissolved in ethanol and the concentrations determined using UV spectrophotometry. Serial dilutions were prepared so that a range of drug concentrations could be tested without changing the final concentration of ethanol (≦0.2%) present in the cell cultures.

Cells

Human promyelocytic leukemia (HL60) cells were grown in RPMI-1640 medium containing 10% fetal bovine serum. The cells were incubated at 37° C. in the presence of 5% $CO_2$.

Assay Conditions

HL60 cells were plated at $1.2 \times 10^5$ cells/ml. Eighteen hours after plating, cells in duplicate were treated with drug. Four days later, the cells were harvested and a nitro blue tetrazolium reduction assay was performed (Collins et al., 1979; J. Exp. Med. 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In Vitro Transcription Assay

Transcription activity was measured in ROS 17/2.8 (bone) cells that were stably transfected with a 24-hydroxylase (24Ohase) gene promoter upstream of a luciferase reporter gene (Arbour et al., 1998). Cells were given a range of doses. Sixteen hours after dosing the cells were harvested and luciferase activities were measured using a luminometer.

RLU=relative luciferase units.

Intestinal Calcium Transport and Bone Calcium Mobilization

Male, weanling Sprague-Dawley rats were placed on Diet 11 (0.47% Ca) diet+AEK oil for one week followed by Diet 11 (0.02% Ca)+AEK oil for 3 weeks. The rats were then switched to a diet containing 0.47% Ca for one week followed by two weeks on a diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium determined as a measure of bone calcium mobilization. The first 10 cm of the intestine was also collected for intestinal calcium transport analysis using the everted gut sac method.

Interpretation of Data

Summary of Biological Findings. This compound Me-Cvit binds the VDR with the same affinity as the native hormone, and can be considered to be equally potent as 1,25$(OH)_2D_3$ in this activity. Me-Cvit also displays approximately 20 times less cell differentiation activity and about 10 times less in vitro gene transcription activity compared to 1,25$(OH)_2D_3$. While this compound has activity comparable to 1,25$(OH)_2$ $D_3$ in vitro, it shows less activity in vivo on bone calcium mobilization compared to the native hormone, and less activity in vivo in promoting intestinal calcium transport compared to the native hormone. Because this compound exhibits relatively significant cell differentiation and transcriptional activity, but relatively low calcemic activity on bone, it might be useful for treating patients with various types of cancers, especially for the treatment of leukemia, colon cancer, breast cancer, skin cancer and prostate cancer. Me-Cvit might not only be useful in the treatment of the above listed cancers, but also in the prevention of the above listed cancers.

Also, because Me-Cvit binds the receptor as well as the native hormone but has markedly lower potency in biological activities downstream from receptor binding, it is possible this compound could act as a dominant negative and be useful as an antidote for vitamin D or analog intoxication. In other words, Me-Cvit may act in vivo as an antagonist against hypercalcemia caused by a vitamin D compound.

VDR binding, HL60 cell differentiation, and transcription activity. Me-Cvit ($K_i = 2 \times 10^{-11}$M) has about the same activity as the natural hormone 1α,25-dihydroxyvitamin $D_3$ ($K_i = 3 \times 10^{-11}$M) in its ability to compete with [$^3$H]-1,25$(OH)_2D_3$ for binding to the full-length recombinant rat vitamin D receptor (FIG. 1). Me-Cvit displays about 2 logs or 20 times less activity ($EC_{50}=8\times10^{-8}M$) in its ability (efficacy or potency) to promote HL-60 cell differentiation as compared to $1\alpha,25$-dihydroxyvitamin $D_3$ ($EC_{50}=2\times10^{-9}M$) (See FIG. 2). Also, compound Me-Cvit ($EC_{50}=4\times10^{-9}M$) has about 1 log or 10 times less transcriptional activity in bone cells than $1\alpha,25$-dihydroxyvitamin $D_3$ ($EC_{50}=2\times10^{-10}M$) (See FIG. 3). These results suggest that Me-Cvit may have significant activity as an anti-cancer agent and may be very effective because it has direct cellular activity in causing cell differentiation, gene transcription, and in suppressing cell growth.

Calcium mobilization from bone and intestinal calcium absorption in vitamin D-deficient animals. Using vitamin D-deficient rats on a low calcium diet (0.02%), the activities of Me-Cvit and $1,25(OH)_2D_3$ in intestine and bone were tested. As expected, the native hormone ($1,25(OH)_2D_3$) increased serum calcium levels at all dosages (FIG. 4). The study reported in FIG. 4 shows that Me-Cvit has little activity in mobilizing calcium from bone and is about 400 times less potent than $1,25(OH)_2D_3$. The administration of 7020 pmol/day of Me-Cvit for 4 consecutive days did not cause mobilization of bone calcium (4.3 mg/dL) but the native hormone $1,25(OH)_2D_3$ had significant activity at 7020 pmol/day where a substantial effect was seen (7.6 mg/dL).

Intestinal calcium transport was evaluated in the same group of animals using the everted gut sac method (FIG. 5). The study reported in FIG. 5 shows Me-Cvit has little intestinal calcium transport activity as compared to $1,25(OH)_2D_3$. Administration of 7020 pmol/day of Me-Cvit for 4 consecutive days resulted in substantially less activity as compared to $1,25(OH)_2D_3$ at the same 7020 pmol/day dosage (4.8 versus 8.3 respectively).

These results show that the compound Me-Cvit promotes intestinal calcium transport in a dose dependent manner. Thus, it may be concluded that Me-Cvit has lower intestinal calcium transport activity to that of $1,25(OH)_2D_3$ at the recommended lower doses.

These results further illustrate that Me-Cvit is an excellent candidate for numerous human therapies as described herein. Me-Cvit is a candidate for treating a cancer because: (1) it has VDR binding, transcription activity and cellular differentiation activity; (2) it has lower risk of hypercalcemic liability, unlike $1,25(OH)_2D_3$; and (3) it is easily synthesized.

Also, because Me-Cvit binds the receptor as well as the native hormone but has markedly lower potency in biological activities downstream from receptor binding, it is possible this compound could act as a dominant negative and be useful as an antidote for vitamin D or analog intoxication. In other words, Me-Cvit may act in vivo as an antagonist against hypercalcemia caused by a vitamin D compound.

For prevention and/or treatment purposes, the compounds of this invention defined by formula I, particularly Me-Cvit, may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds of formula I and particularly Me-Cvit, may be administered orally, topically, parenterally, rectally, nasally, sublingually or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications. A dose of from 0.01 μg to 1000 μg per day of the compounds I, particularly Me-Cvit, preferably from about 0.1 μg to about 500 μg per day, is appropriate for prevention and/or treatment purposes, such dose being adjusted according to the disease to be treated, its severity and the response of the subject as is well understood in the art. Since the compound exhibits specificity of action, each may be suitably administered alone, or together with graded doses of another active vitamin D compound—e.g. $1\alpha$-hydroxyvitamin $D_2$ or $D_3$, or $1\alpha,25$-dihydroxyvitamin $D_3$—in situations where different degrees of bone mineral mobilization and calcium transport stimulation is found to be advantageous.

Compositions for use in the above-mentioned treatments comprise an effective amount of the compounds I, particularly Me-Cvit, as defined by the above formula I and Ia as the active ingredient, and a suitable carrier. An effective amount of such compound for use in accordance with this invention is from about 0.01 μg to about 1000 μg per gm of composition, preferably from about 0.1 μg to about 500 μg per gram of composition, and may be administered topically, transdermally, orally, rectally, nasally, sublingually, or parenterally in dosages of from about 0.01 μg/day to about 1000 μg/day, and preferably from about 0.1 μg/day to about 500 μg/day.

The compounds I, particularly Me-Cvit, may be formulated as creams, lotions, ointments, topical patches, pills, capsules or tablets, suppositories, aerosols, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds I, particularly Me-Cvit, may be advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a

We claim:
1. A compound having the formula:

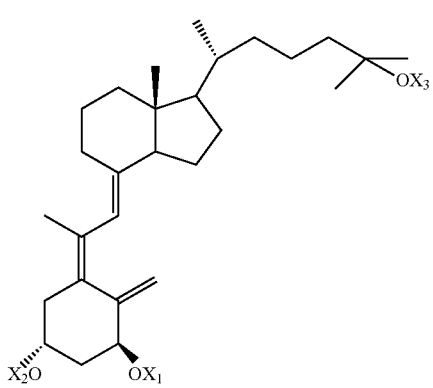

where $X_1$, $X_2$ and $X_3$, which may be the same or different, are each selected from hydrogen or a hydroxy-protecting group.

2. The compound of claim 1 wherein $X_3$ is hydrogen.
3. The compound of claim 1 wherein $X_1$ is hydrogen.
4. The compound of claim 1 wherein $X_1$, $X_2$ and $X_3$ are all t-butyldimethylsilyl.
5. A pharmaceutical composition containing an effective amount of at least one compound as claimed in claim 1 together with a pharmaceutically acceptable excipient.
6. The pharmaceutical composition of claim 5 wherein said effective amount comprises from about 0.01 μg to about 1000 μg per gram of composition.
7. The pharmaceutical composition of claim 5 wherein said effective amount comprises from about 0.1 μg to about 500 μg per gram of composition.
8. 1α,25-dihydroxy-6-methylvitamin $D_3$ having the formula:

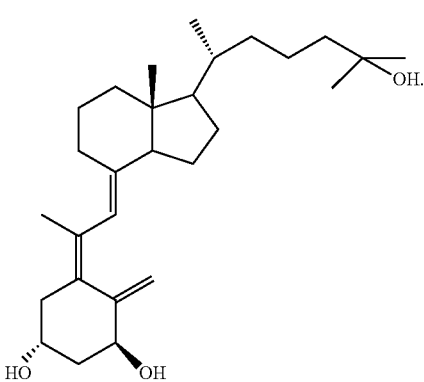

9. A pharmaceutical composition containing an effective amount of 1α,25-dihydroxy-6-methylvitamin $D_3$ together with a pharmaceutically acceptable excipient.

10. The pharmaceutical composition of claim 9 wherein said effective amount comprises from about 0.01 μg to about 1000 μg per gram of composition.

11. The pharmaceutical composition of claim 9 wherein said effective amount comprises from about 0.1 μg to about 500 μg per gram of composition.

12. A method of treating a disease selected from the group consisting of leukemia, colon cancer, breast cancer, skin cancer or prostate cancer comprising administering to a subject with said disease an effective amount of a compound having the formula:

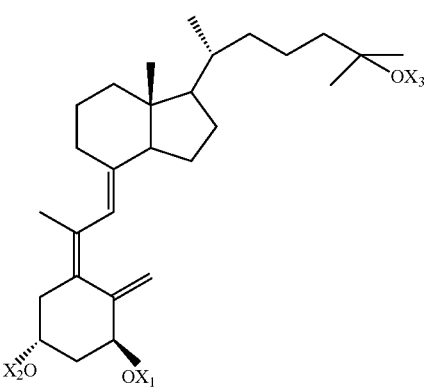

where $X_1$, $X_2$ and $X_3$ which may be the same or different, are each selected from hydrogen or a hydroxy-protecting group.

13. The method of claim 12 wherein the compound is administered orally.
14. The method of claim 12 wherein the compound is administered parenterally.
15. The method of claim 12 wherein the compound is administered transdermally.
16. The method of claim 12 wherein the compound is administered rectally.
17. The method of claim 12 wherein the compound is administered nasally.
18. The method of claim 12 wherein the compound is administered sublingually.
19. The method of claim 12 wherein the compound is administered in a dosage of from about 0.01 μg/day to about 1000 μg/day.
20. The method of claim 12 wherein the compound is 1α,25-dihydroxy-6-methylvitamin $D_3$ having the formula:

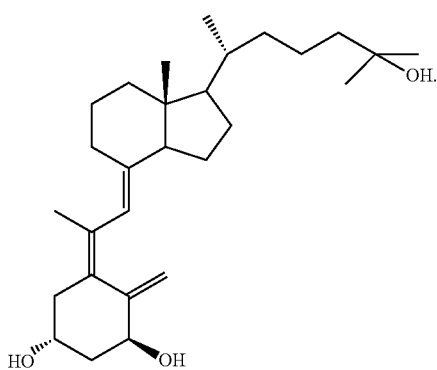

Ia

21. A method of inhibiting development of hypercalcemia comprising administering to a subject an effective amount of a compound having the formula:

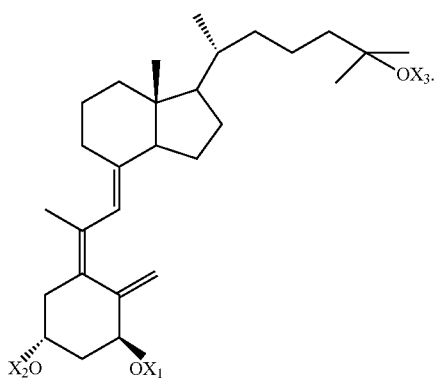

I

22. The method of claim 21 wherein the compound is administered orally.

23. The method of claim 21 wherein the compound is administered parenterally.

24. The method of claim 21 wherein the compound is administered transdermally.

25. The method of claim 21 wherein the compound is administered rectally.

26. The method of claim 21 wherein the compound is administered nasally.

27. The method of claim 21 wherein the compound is administered sublingually.

28. The method of claim 21 wherein the compound is administered in a dosage of from about 0.01 μg/day to about 1000 mg/day.

29. The method of claim 21 wherein the compound is 1α,25-dihydroxy-6-methylvitamin $D_3$ having the formula:

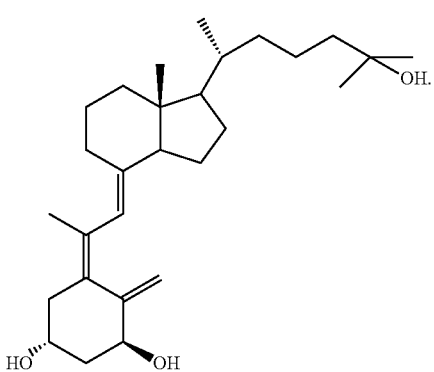

Ia

* * * * *